United States Patent [19]

Clarke

[11] Patent Number: 5,054,487

[45] Date of Patent: Oct. 8, 1991

[54] LASER SYSTEMS FOR MATERIAL ANALYSIS BASED ON REFLECTANCE RATIO DETECTION

[75] Inventor: Richard H. Clarke, Scituate, Mass.

[73] Assignee: Boston Advanced Technologies, Inc., Boston, Mass.

[21] Appl. No.: 474,344

[22] Filed: Feb. 2, 1990

[51] Int. Cl.$^5$ .................. A61B 5/00; G01N 33/48
[52] U.S. Cl. .................... 128/633; 356/39; 250/227.23
[58] Field of Search ............ 356/39, 41, 338; 128/633, 634; 250/339, 343, 227.23

[56] References Cited

U.S. PATENT DOCUMENTS 4,785,814 10/1988 Kane .................. 356/41
4,796,636 1/1989 Brenstetter et al. ........... 128/633
4,854,699 8/1989 Edgar Jr. .................. 128/633

Primary Examiner—Davis L. Willis
Assistant Examiner—La Charles P. Keesee
Attorney, Agent, or Firm—Thomas J. Engellenner

[57] ABSTRACT

Systems and methods for non-invasive material analysis are disclosed in which a material (e.g., a liquid such as blood) is illuminated at a plurality of discrete wavelengths. Measurements of the intensity of reflected light at such wavelengths are taken, and an analysis of reflection ratios for various wavelengths is performed. Changes in the reflection ratios can be correlated with specific material properties such as the concentration of analytes (e.g., oxygen content, glucose levels, cholesterol or drugs in a subject's circulatory system).

11 Claims, 4 Drawing Sheets

LASER SYSTEMS FOR MATERIAL ANALYSIS BASED ON REFLECTANCE RATIO DETECTION

BACKGROUND OF THE INVENTION

The technical field of this invention is material analysis and, in particular the invention relates to the detection and quantification of analytes in materials by measuring reflectivity at multiple wavelengths.

Material analysis, especially the analysis of liquid materials for the presence of solutes, can be a tedious and complex task. In many instances it would be more desirable to be able to analyze materials quickly, easily, and non-invasively. One example of such an application is blood analysis.

Conventionally, blood is analyzed by withdrawing a sample from the body of a subject and examining it using one or more techniques such as immunoassays, activity assays, chromotographic assays, and spectrophotometric assays. These conventional methods all suffer from several common disadvantages. One such disadvantage is that it usually takes some time to perform tests on the sample, the length of time being dependent on the complexity of the test. This time delay between when the blood is drawn and when the analysis is completed provides a window during which the subject's blood content may have changed, leading to erroneous test results.

Additionally, situations arise when repeated or even continuous blood monitoring is desirable, for example when monitoring drug dosage changes or glucose level variations. In addition to the stale date problem discussed above, another disadvantage is that such repeated invasive blood sampling can cause discomfort to the subject being monitored. A further disadvantage to conventional blood testing techniques is that the people drawing and testing the blood sample are put at risk for exposure to infectious disease agents.

Accordingly, it is the object of the present invention to provide an analytic apparatus for non-invasively, quickly, and easily detecting and quantifying analytes in a material.

It is another object of this invention to provide an analytic apparatus particularly adapted for detecting and quantifying analytes in blood in such a way as to avoid the problems of stale test results, subject discomfort, and potential technician exposure to infectious agents.

It is also an object of the invention to provide a system that reduces the number of blood samples which must be drawn from patients who require repeated blood testing to evaluate such parameters as drug dose changes or glucose level variations, and to permit continuous analysis of blood within the circulatory system where desirable.

SUMMARY OF THE INVENTION

Systems and methods for material analysis are disclosed in which a material (e.g., a liquid such as blood) is illuminated at a plurality of discrete wavelengths. Measurements of the intensity of reflected light at such wavelengths are taken, and an analysis of reflection ratios for various wavelengths is performed. Changes in the reflection ratios can be correlated with specific material properties such as the concentration of analytes (e.g., oxygen content, glucose levels, cholesterol or drugs in a subject's circulatory system).

In one aspect of the invention, an analytic apparatus and method are described employing a multi-wavelength illumination source, a wavelength specific detector array, and a reflection ratio analyzer. The illumination source illuminates a material sample at a plurality of discrete wavelengths. The detector array detects the light reflected from the sample, converts the detected light into electrical signals indicative of the intensity of the reflected light at each wavelength, and transmits the converted signals to a reflection ratio analyzer. The reflection ratio analyzer then derives a reflectance ratio for at least two of the detected wavelengths, such that the ratio can be compared with predetermined values to detect the presence and/or concentration of an analyte in a material sample.

In one illustrated embodiment of the invention the illumination source further comprises at least two laser diodes, producing light at distinct wavelengths, spanning at least a portion of a spectrum from about 500 nm to about 2000 nm, preferably from about 600 nm to about 1500 nm. This embodiment is particularly well suited to provide a system for detecting analytes in blood circulating through a surface vein due to the penetration of near infrared wavelengths of light through human skin.

The present invention is an improvement over the prior art in that it can non-invasively, quickly and easily detect and/or quantify analytes in blood and other material samples. In this way, the invention eliminates the problems of stale test data, subject discomfort and potential exposure to infectious diseases.

The invention will next be described in connection with certain Preferred embodiments; however, it should be clear that various additions, subtractions and modifications can be made without departing from the spirit or scope of the invention. For example, although the invention is illustrated in connection with a blood analysis system, various alternative embodiments can also be devised, such as systems for monitoring liquid foodstuffs, oils, beverages, chemicals and the like. Additionally, the invention can be used to monitor analytes in non-liquid or semiliquid materials, for example to monitor freshness of meats and other foods.

Although the illustrated embodiment shows a system with a fiber optic bundle for delivery of six distinct wavelengths of light, it should be clear that the number of interrogation wavelengths, the size and shape of the sampling head and the means for transmitting the light to and from the sample can be varied to meet particular needs and applications. In particular, a single fiber can be used for transmission and detection of multiple interrogation wavelengths. Moreover, although lasers are described as preferred light sources, other illumination means including non-coherent, discrete wavelength light sources can be employed.

DETAILED DESCRIPTION

Figure 1:
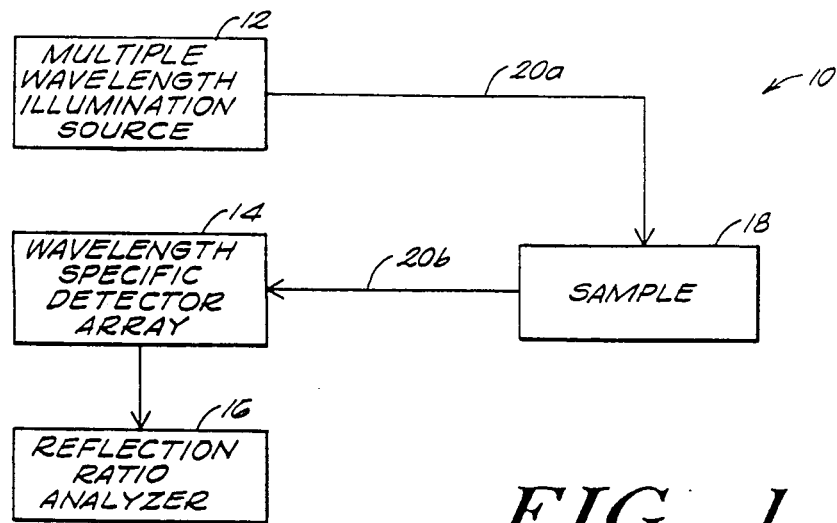
FIG. 1 is a schematic block diagram of an analytic apparatus according to the invention.

A schematic block diagram of an analytic apparatus 10 according to the invention is shown in FIG. 1. Apparatus 10 includes a multiple wavelength illumination source 12, a wavelength specific detector array 14, and a reflection ratio analyzer 16. Illumination source 12 can be a single multi-wavelength laser diode or a series of discrete diode elements, each emitting a distinct wavelength of light. Source 12 illuminates the material sample 18 at a plurality of wavelengths via optical path 20a. Detector array 14 detects light reflected from sample 18 through optical path 20b. The detector array 14 converts the reflected light into electrical signals indicative of the intensity of the reflected light at each wavelength and transmits the converted signals to the reflection ratio analyzer 16 which processes the electrical signals and derives a reflectance ratio for at least two of the wavelengths transmitted. Analyzer 16 then compares the calculated reflectance ratio with predetermined values to detect the presence of an analyte in the material sample 18.

Figure 2:
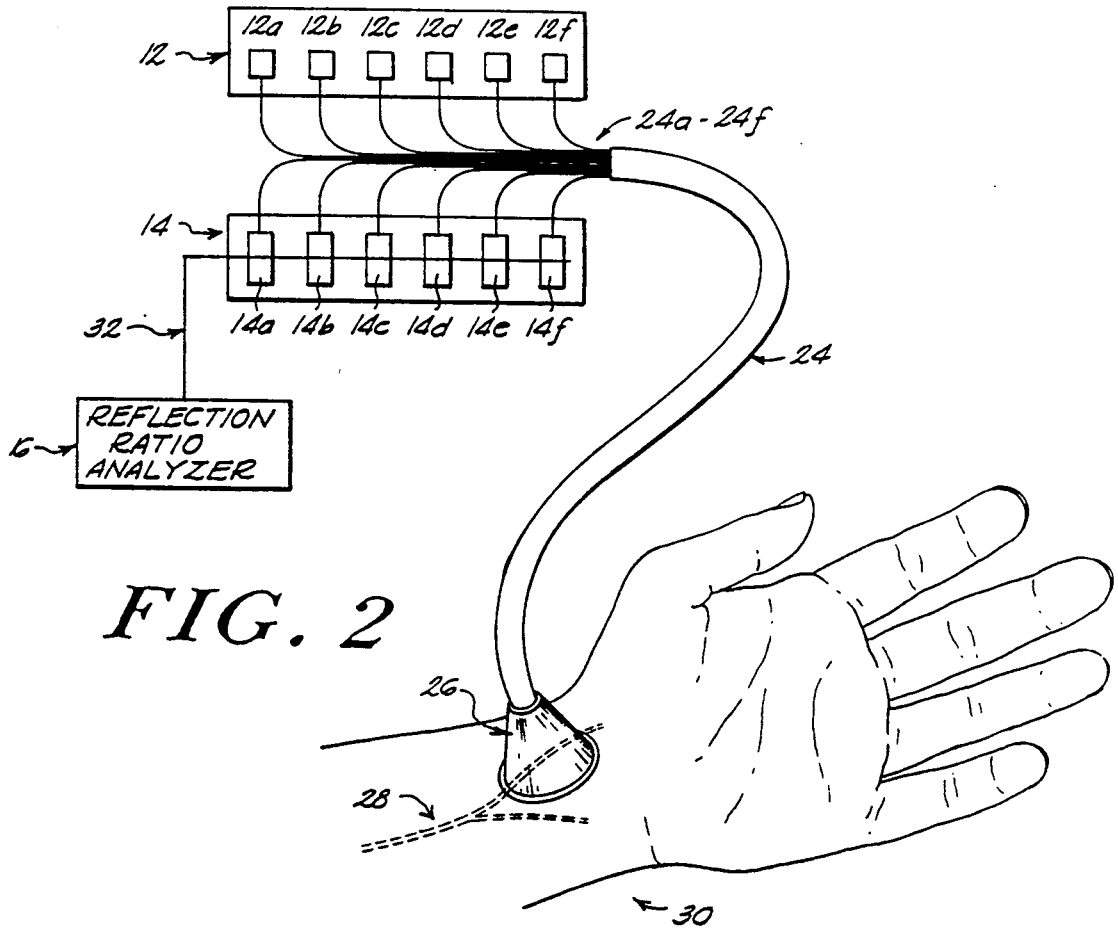
FIG. 2 is a schematic diagram of the apparatus according to the invention particularly adapted for non-invasive detection of analytes in a subject's blood.

An analytic apparatus 10 according to the invention particularly adapted to provide a system for detecting analytes in blood circulating through a surface vein is shown in FIG. 2. As can be seen from FIG. 2, laser diode elements $12a-12f$ comprise a multiple wavelength illumination source 12 which provides light at a series of skin penetrating wavelengths (e.g. from about 500 nm to about 2000 nm). Diode elements $12a-12f$ each transmit a predetermined wavelength of light via corresponding optical fiber elements $24a-24f$ and sampling head 26, to vein segment 28 of wrist 30. (Alternatively, light at various wavelengths can be emitted by one multiple-wavelength laser diode and transmitted via a single optical fiber.) The discrete wavelengths of laser light automatically pass through the tissue of wrist 30 and illuminate the blood circulating in surface vein 28.

A fraction of the transmitted light is reflected back from the blood circulating in surface vein 28 along optical fiber elements $24a-24f$. (Each optical fiber element $24a-24f$ carries a reflected light signal having the same wavelength as the light originally transmitted along it.) Diode detectors $14a-14f$ receive the reflected light from the optical fiber elements $24a-24f$ and convert these light waves into a series of electrical signals indicative of the intensity of each of the reflected wavelengths of light received from surface vein 28. For example, if laser diode element 12a originally transmitted light of wavelength 500 nm along optical fiber element 14a, then optical fiber element 14a will carry reflected light of wavelength 500 nm back to diode detector element 22a.

As shown in FIG. 2 diode detector elements $14a-14f$ transmit the electrical signals indicative of the intensity of the reflected light to reflection ratio analyzer 16 along electrical connection 32. Analyzer 16 compares the electrical signals received from diode detector elements $14a-14f$ to derive a reflectance ratio for at least two of the transmitted wavelengths of light, such that the ratio can be compared to predetermined values to detect the presence of an analyte in the blood flowing through vein 28. Analyzer 16 can also comprise means for quantifying the concentration of the detected analyte.

Figure 3:
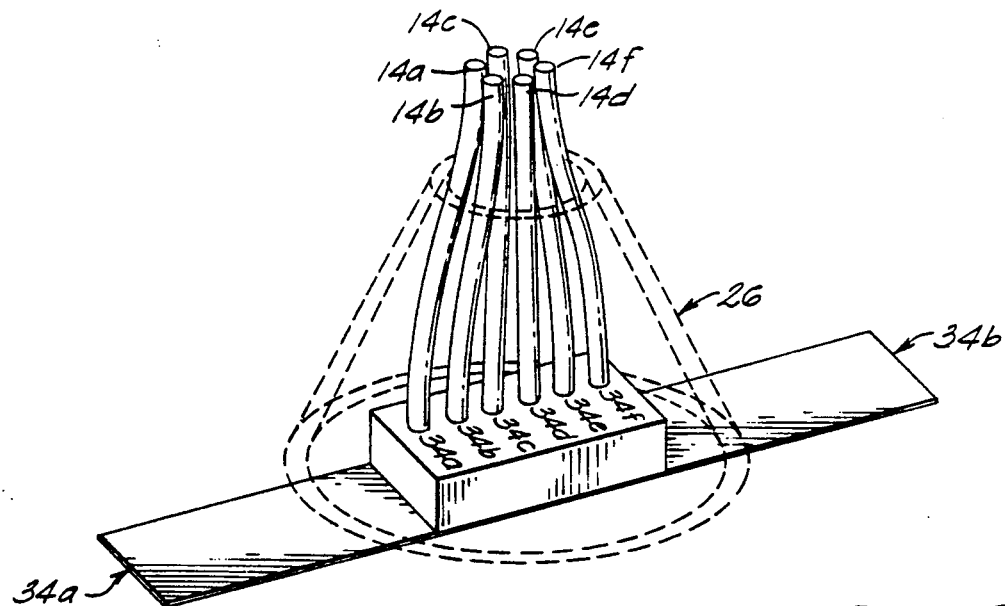
FIG. 3 is a detailed view of the sampling head assembly of the apparatus of FIG. 3.

FIG. 3 shows a more detailed view of the sampling head 26 of FIG. 2. As can be seen from FIG. 3, optical fiber elements $24a-24f$ of optical fiber bundle 24 are adapted to extend through a corresponding set of holes $32a-32f$ in the sampling head 26 thus facilitating alignment of optical fiber elements $24a-24f$ along surface vein 28. Sampling head 26 also comprises taping flanges 34a and 34b located at opposed ends of sampling head 26, providing a means for affixing sampling head 26 above surface vein 28.

Figure 4:
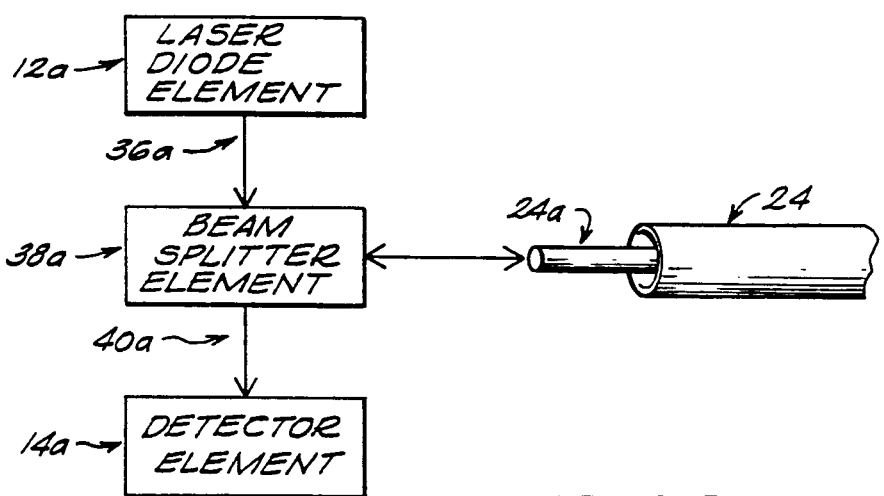
FIG. 4 is a more detailed illustration of an individual optical fiber and its connection to an illumination source and a detector element according to the invention.

FIG. 4 is a more detailed illustration of an individual optical fiber 24a and its connection to an illumination source 12a and a detector element 14a according to the invention. Since each of optical fiber elements $24a-24f$ is identically adapted, only optical fiber element 24a is shown. Laser diode element 12a is connected to optical fiber element 24a via optical fiber element 36a through optical splitter 38a. Diode detector element 14a is connected to optical fiber element 24a via optical fiber element 40a, also through optical splitter 38a. Optical splitter element 38a (and corresponding elements $38b-38f$, not shown) enable dual usage of optical fiber elements $24a-24f$ so that the light transmitted from laser diode elements $12a-12f$ and the light reflected back from surface vein 28 travels along the same optical fiber elements $24a-24f$.

Figure 5:
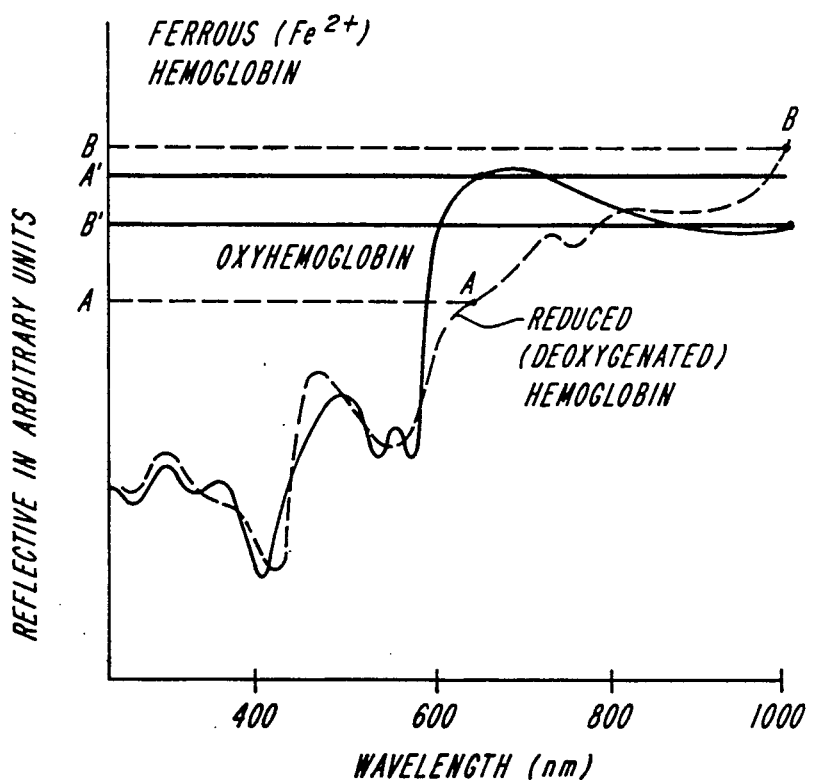
FIG. 5 is a graph of the reflectance spectrum of nonoxygenated and fully oxygenated blood, illustrating the analytical techniques of the present invention.

FIG. 5 is a graph of the reflectance spectra of deoxygenated (shown by dashed curve) and fully oxygenated (shown by solid curve) hemoglobin. The wavelength of source light is shown along the x-axis and the intensity of the light reflected back from the hemoglobin is shown along the y-axis. Considering the measured ratio of the reflected light for deoxygenated hemoglobin and oxyhemoglobin at wavelengths of 650 nm and 1000 nm, and referring to FIG. 5, the intensity of the reflected light measured at 650 nm (shown by point A) divided by the intensity of the reflected light measured at 1000 nm (shown by point B) in the case of deoxygenated hemoglobin is less than one. However, in the case of oxyhemoglobin, the same ratio (shown by corresponding points A' and B') is greater than one. Such a clearly differentiable ratio is readily detectable, and the exact ratio can be correlated with the actual oxygen content of the blood sample under analysis.

Figure 6:
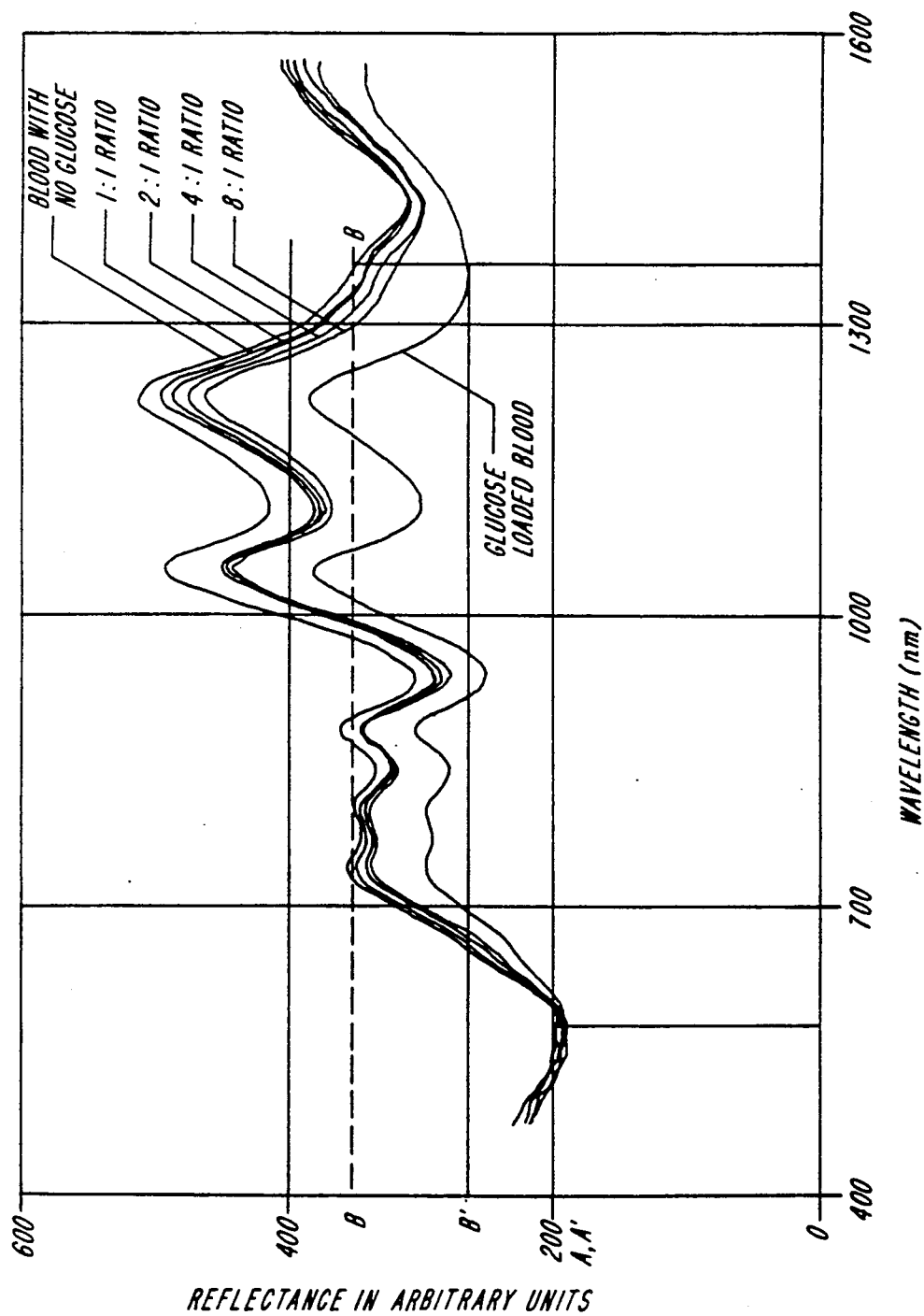
FIG. 6 is a graph of the reflectance spectrum of blood containing various concentrations of glucose, further illustrating the analytical techniques of the present invention.

FIG. 6 is a graph of the reflectance spectra of blood containing varying amounts of sugar (glucose). Again, the wavelength of the source light is shown along the x-axis, and the intensity of the light reflected back from the blood is shown along the y-axis. In this instance, the ratio of the measured reflected light by blood, for example, containing no glucose at about 570 nm (shown by point A) and at about 1350 nm (shown by point B) can be compared with the reflectance values obtained from samples containing various amounts of glucose. As shown in FIG. 6, blood loaded with a defined amount of glucose exhibits a nearly identical reflectance intensity at about 570 nm (shown by point A') but a substantially different reflectance at about 1350 nm (shown by point B').

Systematic dilutions of the glucose-loaded blood sample were also undertaken and reflectance spectra were measured. As shown in FIG. 6, differences in the reflectance ratio at the chosen wavelengths can be readily determined and correlate well with the analyte (in this case, glucose) concentrations in the blood sample under analysis.

While FIGS. 5 and 6 illustrates the invention as applied to detection of oxygen and sugar in blood, in alternative embodiments the invention is suitable for analyzing various other analytes in blood, including cholesterol, insulin, biological factors, and drugs, as well as detecting the components of other materials, such as contaminants in cooking oils, moisture in fuels, alcohol content in beverages, and food adulteration.

As indicated above, the invention may be embodied in other specific forms without departing from the spirit or the essential characteristics thereof. The present embodiment is to be considered as illustrative and not restrictive. The scope of the invention is indicated by the appended claims, rather than by the foregoing description, and all changes which come within the meaning and range of equivalent of the claims are therefore intended to be embraced therein.

What is claimed is:

1. An apparatus for detecting non-oxygen analyte in a subject's blood, the apparatus comprising:
    illumination means for generating illuminating light at a plurality of distinct wavelengths, said light having an intensity sufficient to non-invasively illuminate blood circulating in a blood vessel below the surface of a subject's skin, the plurality of wavelengths further comprising at least one wavelength further at which the reflectance of the light is substantially uneffected by the concentration of said analyte in the blood, and at least one infrared wavelength at which the reflectance varies with the concentration of said analyte in the blood;
    detector means for non-invasively detecting light reflected from the material at said plurality of wavelengths and for converting said detected light into electrical signals, said signals being indicative of the intensity of said reflected light at each wavelength;
    sampling means for optical delivery of said illuminating light to a subject's skin, including affixation means for affixing a sampling head to said skin and alignment means for optically aligning the illuminating means with a blood vessel below the surface of the skin;
    at least one optical fiber means for transmitting illuminating light for the illumination means to the sampling means and for the illumination means to the sampling means and for returning reflected light from the sampling means to the detector means; and
    analyzing means for non-invasively receiving and comparing said electrical signals to derive a reflectance ratio for at least two of said wavelengths, such that said ratio can be compared with predetermined values to non-invasively detect the presence of said analyte in said material.

2. The apparatus of claim 1 wherein said illumination means further comprises at least two laser diodes, producing light at distinct wavelengths.

3. The apparatus of claim 1 wherein said wavelengths of light generated by said illumination means span at least a portion of a spectrum from about 500 nm to about 2000 nm.

4. The apparatus of claim 1 wherein said wavelengths of light generated by said illumination means span at least a portion of a spectrum from about 600 nm to about 1500 nm.

5. The apparatus of claim 1 wherein said analyzing means further comprises means for quantifying the concentration of said analyte in said material.

6. A method for detecting a non-oxygen analyte in circulating blood, the method comprising:
    non-invasively generating illuminating light at a plurality of distinct wavelengths, said light having an intensity sufficient to non-invasively illuminate blood circulating in a blood vessel below the surface of a subject's skin, the plurality of wavelengths further comprising at least one wavelength at which the reflectance of the light is substantially unaffected by the concentration of said analyte in the blood, and at least one infrared wavelength at which the reflectance varies with the concentration of said an analyte in the blood;
    delivering said illuminating light to a material comprising a subject's skin via a sampling means affixed to said skin, such that a blood in a blood vessel below the surface of the skin is illuminated;
    non-invasively detecting light reflected from said blood and converting said detected light into electrical signals indicative of the intensity of said reflected light at a plurality of wavelengths;
    non-invasively analyzing said electrical signals to derive a reflectance ratio for at least two of said wavelengths; and
    non-invasively comparing said ratio to a predetermined value to detect the presence of an analyte in said blood.

7. The method of claim 6 wherein the step of illuminating said material further includes illuminating said material at a plurality of wavelengths spanning at least a portion of a spectrum ranging from about 500 nm to about 2000 nm.

8. The method of claim 6 wherein the step of illuminating said material further includes illuminating said material at a plurality of wavelengths spanning at least a portion of a spectrum ranging from about 600 nm to about 1500 nm.

9. The method of claim 6 wherein the step of illuminating said material further comprises illuminating a liquid sample.

10. The method of claim 6 wherein the step of illuminating said material further comprises non-invasively illuminating a tissue region of said subject containing blood to monitor the composition of said blood.

11. The method of claim 6 wherein the step of analyzing said signals further comprises quantifying the concentration of an analyte in said material.

* * * * *

UNITED STATES PATENT AND TRADEMARK OFFICE
CERTIFICATE OF CORRECTION

PATENT NO. : 5,054,487

DATED : October 8, 1991

INVENTOR(S) : Richard H. Clarke

It is certified that error appears in the above-identified patent and that said Letters Patent is hereby corrected as shown below:

In claim 1, at column 5, line 38, "material" should read --blood--.

In claim 1, at column 5, line 51, delete "for the illumination means to the sampling means and".

In claim 1, at column 5, line 52, "for" should read --from--.

In claim 1, at column, line 62, "material" should read --blood--.

In claim 5, at column 6, line 14, "material" should read --blood--.

UNITED STATES PATENT AND TRADEMARK OFFICE
CERTIFICATE OF CORRECTION

PATENT NO. : 5,054,487

DATED : October 8, 1991

INVENTOR(S) : Richard H. Clarke

It is certified that error appears in the above-identified patent and that said Letters Patent is hereby corrected as shown below:

In claim 11, at column 6, line 61. "material" should read --blood--.

Signed and Sealed this

Seventh Day of December, 1993

Attest:

BRUCE LEHMAN

Attesting Officer — Commissioner of Patents and Trademarks